United States Patent [19]

Courbon

[11] Patent Number: 4,737,171
[45] Date of Patent: Apr. 12, 1988

[54] PORTABLE INDIVIDUAL DUST COLLECTOR

[75] Inventor: Paul Courbon, Apremont, France

[73] Assignee: Charbonnages de France, Paris, France

[21] Appl. No.: 892,910

[22] Filed: Aug. 1, 1986

[30] Foreign Application Priority Data

Aug. 5, 1985 [FR] France .................. 85 11941

[51] Int. Cl.⁴ .................................. B01D 45/12
[52] U.S. Cl. .................................. 55/270; 73/28; 73/863.21
[58] Field of Search ............ 55/270; 73/28, 863.21, 73/863.23

[56] References Cited

U.S. PATENT DOCUMENTS

| | | | |
|---|---|---|---|
| 3,590,629 | 7/1971 | Courbon | 55/270 X |
| 3,765,155 | 10/1973 | Courbon | 55/270 |
| 3,949,594 | 4/1976 | Treaftis et al. | 55/270 X |
| 3,953,182 | 4/1976 | Roth | 55/446 X |
| 4,152,923 | 5/1979 | Courbon | 55/270 X |
| 4,178,794 | 12/1979 | Jugle et al. | 55/270 X |
| 4,277,259 | 7/1981 | Rounbehler et al. | 55/270 |
| 4,323,375 | 4/1982 | Chang | 55/270 |
| 4,350,507 | 9/1982 | Greenough et al. | 55/270 |
| 4,461,183 | 7/1984 | Wedding | 55/270 X |
| 4,534,230 | 8/1985 | Courbon | 73/28 X |

FOREIGN PATENT DOCUMENTS

| | | | |
|---|---|---|---|
| 102870 | 3/1984 | European Pat. Off. | 73/28 |
| 2086984 | 12/1971 | France . | |

*Primary Examiner*—Robert Spitzer
*Attorney, Agent, or Firm*—Cushman, Darby & Cushman

[57] ABSTRACT

A portable individular dust collector has a cover which surrounds a rotatable cup. A hood is supported on the cover and houses a prefiltration unit carrying an auxiliary cup containing a filtering foam. The prefiltration unit and said hood define an external peripheral space which is in communication with an annular volume provided beneath said prefiltration unit around a central air inlet in the direction of the rotatable cup to retain the coarser particles of dust.

11 Claims, 2 Drawing Sheets

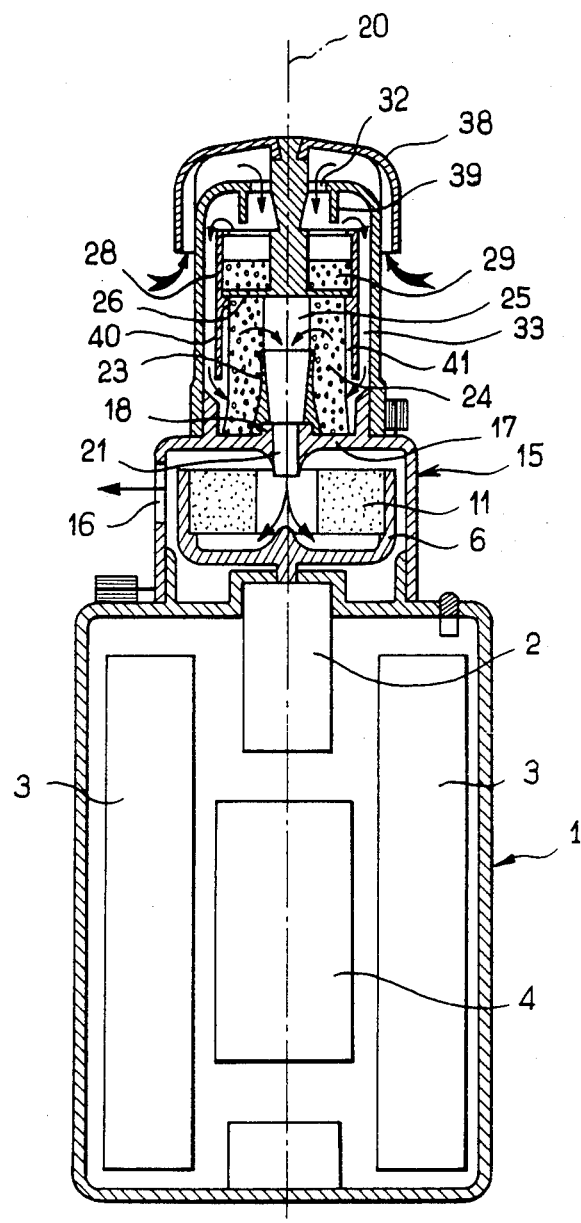
FIG_2

PORTABLE INDIVIDUAL DUST COLLECTOR

FIELD OF THE INVENTION

The present invention relates to a portable individual dust collector which any person can carry on him or her to collect from the atmosphere any suspended dust and to hold said dust for subsequent analysis.

This collector is of the same type as that described in document FR-A-2 531 534. The collector is designed to retain dust of particle sizes such that it is able to enter into the alveoli of the lungs of the person carrying it and to be retained therein. With the aid of this collector it is possible to estimate and even meter the amount of dust said to be breathable which a person may have inhaled during a given period.

The collector described in the above-mentioned document is satisfactory, but it has been noted during its use that it is difficult for it to function properly in heavily dust-laden atmospheres or in an atmosphere which contains a high amount of dust of particle sizes greater than that of breathable dust.

Indeed, this collector is fitted with a filter unit in which the dust is retained which is regarded as breathable and the particle size of which is below 5 microns, as is generally admitted. This filter unit is preceded by a prefiltration unit intended to hold dust the particle size of which is greater than 5 microns. In other words, the prefiltration unit effects in the dust suspended in the surrounding medium, sucked in by the collector, a cutting-off in the manner of a low-pass filter in such a manner as to allow only those particles of dust to reach the filtration unit which are included in the range below 5 microns. In the above-mentioned document it has been pointed out that the filtration unit holds the dust the particle size of which ranges from 0.5 to 5 microns because it is also admitted that dust of particle size below 0.5 micron is too fine to be retained by the filtering unit and probably also by the lungs. The values indicated are of relative importance and the collector may be easily adapted to ranges of values that are different.

It has been found in use that the very design of the collector which is the subject of the above-mentioned document has a drawback when the collector is used in an atmosphere laden with numerous types of dust the particle size of which is greater than 5 microns or other comparable value which would be entertained as cut-off value for the prefiltration unit. Indeed, it is observed in this case that the collector is choked more or less rapidly by the coarser dust.

It is an object of the invention to cope with this situation and to provide a general design of an individual dust collector of the type defined hereinabove able to separate and to hold a high amount of dust of particle size greater than a determine cut-off value.

It is a secondary object of the invention to arrive at an overall design of an individual dust collector possessing the advantages explained hereinabove able to be easily adapted, as a result of its very design, to an amount much greater than the initially envisaged amount of dust of particle size greater than the cut-off value provided for.

SUMMARY OF THE INVENTION

In a portable individual collector for dust likely to be retained in the lungs, with a cover having a generally longitudinal axis, with a central air inlet and at least a lateral air outlet, a cup mounted to be rotatable around said axis inside the cover and containing a crown of filtering foam with central air inlet channel, a hood capping the central air inlet of the cover and ending in an outermost wall with central air input, said hood containing a prefiltration unit disposed upstream of the central air inlet of the cover and ending in a first outermost face away from the cover, the improvement according to the invention provides that the prefiltration unit has a central passage opening connected to the central air inlet of the cover, and said prefiltration unit is supported inside the hood and allowing an external peripheral space to be free from said hood, while the first outermost face of this prefiltration unit is fitted with a gas-proof impact wall which seals the inlet of the central passage opening.

Preferably, the pefiltration unit is shaped and supported to define with the cover and with the hood an annular space which communicates with the peripheral space and which surrounds the central passage opening connected with the central air inlet.

According to an embodiment, the outermost face of the cover is provided with a central boss through which the central passage is provided, connected with the central opening of the air passage of the prefiltration unit, said central boss being in the transversal direction smaller than the hood. The prefiltration unit is supported by said central boss. When the above-mentioned annular volume is present, it is limited in a transversal direction by the central boss and the hood, and in a longitudinal direction by the cover and by the prefiltration unit.

Preferably, the gas-proof impact wall is a wall provided with a raised peripheral edge extending longitudinally opposite the filter foam crown.

According to a further embodiment of the invention, this peripheral edge is continued as a hollow cylinder in the direction of the cover, in the above-mentioned peripheral space, over a substantial fraction of the length in an axial direction of the prefiltration unit, and surrounding the latter without being in contact with it.

Advantageously, the central opening of the hood has, passing freely through it, a rod which extends outwards passing through this opening from the impact wall and this rod has at its external free end a mask which extends before the outermost face of the hood. The crown of filtering foam is contained in the rotating cup defining a free volume with the bottom of said cup.

Preferably, the internal face of the outermost wall of the hood has an internal extension with a concave curved flank which extends concentrically with said central passage inside the central channel of the filtering foam crown, while the inner face of the cup also has a protruding part with a concave curved flank which extends into the central channel coaxially with the filtering foam crown.

BRIEF DESCRIPTION OF THE DRAWINGS

For a better understanding of the improvement made to the portable individual collector, and so that its advantages may be appreciated, preferred embodiments of the invention will hereinafter be described by way of example, with reference to the accompanying drawings, in which:

FIG. 2 is a view similar to that of FIG. 1 of an alternative embodiment.

EMBODIMENT OF PREFERRED EMBODIMENTS

Figure 1:
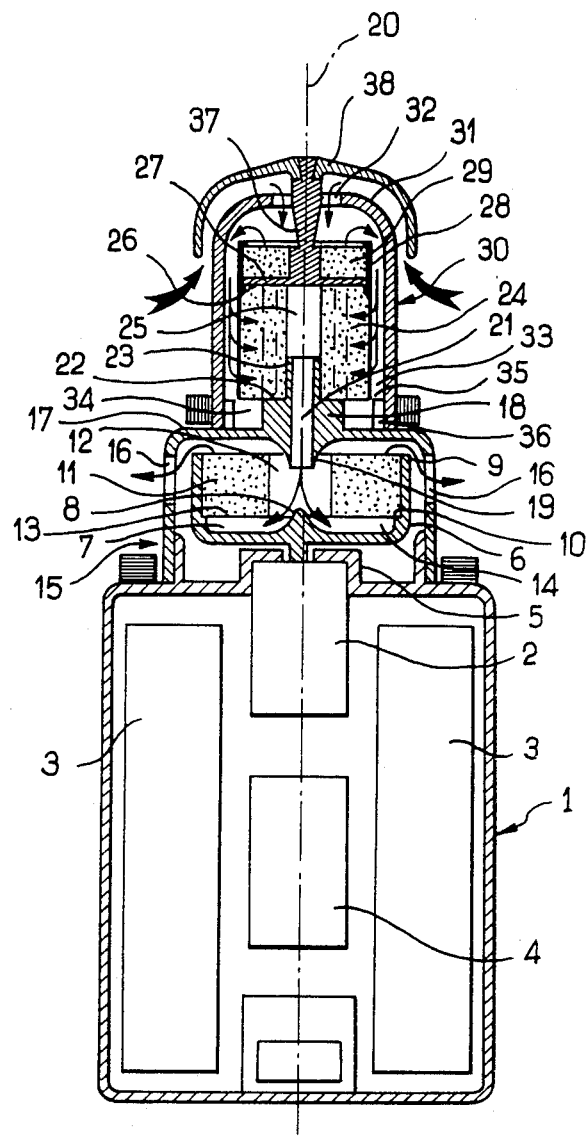
FIG. 1 is an elevation sectional view taken along a plane passing through the general axis of an improved individual collector according to the invention.

The collectors illustrated in FIGS. 1 and 2 each have a structure similar to that of the collector described in the above-mentioned French patent application, and the disclosure in this French document is incorporated therein by reference. Accordingly, a detailed description will be given only of the improvement to the collector attributable to the present invention relative to the surrounding parts.

A hollow body 1 houses a motor 2, electric power sources 3 and a regulation circuit 4. The shaft of the motor 2 extends out of the body 1 through a bearing 5 and, at its free end, it carries a rotatable cup 6 open in a direction opposite to the body 1. The inner face 7 of the bottom of this cup 6 has a central projection 8 with a concave curved flank which connects with said inner surface 7. The inner face 9 of the side wall of said cup 6 has a circular shoulder 10 extending from the inner face 7 of the bottom. A crown 11 of filtering foam having a central channel 12 is contained in the cup 6. The crown 11 extends between the outermost free edge of the shoulder 10 so that a space 14 is defined between the outermost face 13 of the crown 11 and the inner face 7 of the bottom. The central projection 8 extends further than the transversal plane which contains the shoulder 10 so that it enters the inside of the central channel 12.

The assembly constituted by the cup 6 and the crown 11 is enclosed in a cover 15 which is fixed to the body 1 in removable manner. This cover 15 has in its side wall air outflow holes 16, and its outermost wall 17 away from the body 1 has an external central boss 18. The inner face of this outermost wall 17 has, opposite the boss 18, an inner extension 19 having a concave curved flank which extends within the central channel 12 of the crown 11. Alternatively, the central boss 18 could be an insert.

The body 1 and the cover 15 have an overall longitudinal axis 20 shown in dash-dot lines around which there are also disposed, coaxially, the rotatable cup 6 with the central projection 8, the crown 11 and its central channel 12, the cover 15 with the boss 18, and the extension 19. The latter two parts, i.e. the boss 18 and the extension 19 have a central passage 21 extending through them, the axis of which is coincident with the axis 20.

The central boss 18 ends in a flat outermost face 22 and a protruding internal edge 23 which surrounds the central passage 21. This flat face 22 and this internal edge 23 are used to hold in position a prefiltration unit 24 made preferably of filtering foam, which has a central passage opening 25 in which the protruding internal edge 23 fits. Opposite its outermost face by means of which it is supported by the central boss 18, the prefiltration unit 24 ends in an outermost face 26 which is covered by a gas-tight impact wall 27 which seals off the inlet of the central passage opening 25. This impact wall could be a simple disc fixed, for example, by means of an adhesive, to the outermost face 26. Preferably, the impact wall 27 has an external edge extending in the longitudinal direction to define an auxiliary cup 28 the hollow volume of which faces away from the prefiltration unit 24. Advantageously, this auxiliary cup 28 also contains a filtering foam 29.

The assembly which has just been described and which is supported by the central boss 18 is contained within a hood 30. The free outermost edge of the hood 30 is applied against the external face of the outermost wall 17 of the cover 15 to which it is removably fixed in removable manner. This hood 30 is coaxial with the general axis 20 and it ends opposite the cover 15 in an outermost wall 31 in which a central opening 32 concentric with the general axis 20 is provided.

The internal diameter of the hood 30 is greater than the outer diameter of the filtration unit 24 and, accordingly, than the outer diameter of the auxiliary cup 28. Consequently, there is around the filtration unit 24 an outer peripheral space 33 which the air sucked in through the central opening 32 is formed to follow after having flowed around the auxiliary cup 28.

The central boss 18 has a dimension in the longitudinal direction and a dimension in the trasverse direction relative to the general axis 20 such that an annular space 34 is defined around said boss 18, within the hood 30, between the prefiltration unit 24 and the outermost wall 17 of the cover 15. This space 34 is in communication with the peripheral space 33 by means of an annular passage 35. Advantageously, the passage 35 is obtained by means of a collar 36 which is carried by the outer face of the outermost wall 17 of the cover 15, concentrically with the central boss 18. The hood 30 is threaded and adjusted onto said collar 36, the hood being then fixed with screws. By a suitable choice of dimensions it is possible to obtain between the annular volume 34 and the peripheral space 33 an annular passage 35 comparable with a throttling delimited by the collar 36 and the filtration unit 24 placed in position.

In this example, the impact wall which is also the bottom of the auxiliary cup 28 bears a rod 37 which passes through the central opening 32 of the hood 30 and which carries a mask 38 at its external free end. This mask extends in front of the outermost face of the hood 30. It is substantially developed in a direction transverse to the general axis 20 to prevent air from entering directly through the central opening 32 and to force the air to follow a tortuous path.

The collector of the invention operates in the same manner as the collector of the French document referred to hereinabove, but its new design supplies the following appreciable advantages.

When the cup 6 is rotated by the motor 2 it expels, by a centrifugal effect, air through the air outlet holes 16 of the cover 17 and it produces a suction in the direction of the general axis 20. The air sucked in enters through the central opening 32. The gas-tight wall 27 ensures that air cannot directly enter the prefiltration unit 24, but that it must perform a first radial change of direction, and then a second longitudinal change of direction to follow the outer peripheral space 33. The use of the auxiliary cup 28, the bottom of which constitutes the gas-tight impact wall 27, permits full use to be made of the effect of these changes of direction.

The coarser particles in the dust change direction less easily and they enter the auxiliary cup 28 and collide with the impact wall 27. This wall, and the whole of the inner face of the auxiliary cup 28 could be coated with a layer of grease able to hold dust. It is preferable to line the inside of the auxiliary cup 28 with a filtering foam 29 in which a substantial part of the coarser dust particles are retained.

When the air has reached the outer peripheral space 33 it is forced to go through the prefiltration unit 24 following a substantially radial path, so as to reach the central passage opening 25. It undergoes a new change of direction. As it is preferably to use the collector with its general axis 20 vertically disposed, as shown in the figure, this change of direction and the action of gravity together ensure that coarser dust particles which have not been retained by the auxiliary cup 28 and the filtering foam 29, fall into the annular volume 34. The throttled annular space 35 is wide enough to let the particles through, but it brakes their outflow in large quantities should it happen that the collector is overturned.

The foregoing explanation shows that the collector is able to operate in a heavily dust-laden atmosphere and to retain a substantial volume of so-called non-breathable dust before the air reaches the filtering foam crown 11. In addition, the very design of the collector enables it to adapt it in advance, without substantial modification of its structure, to a specific dusty atmosphere. The above-described example is that of the adaptation of the collector to the most heavily dust-laden atmosphere.

The use of the impact wall 26 and the changes of direction resulting therefrom already supply appreciable results. The conversion of this impact wall 26 into an auxiliary cup 28 increases the effect of retention of coarser dust particles. The filtering foam 29 enclosed in the cup further improves this effect. The foam 29 may be chosen so that it preferably retains dust of particle sizes greater than a given value. Generally, a foam with open pores of grade 45 (i.e. 45 cells per length of 25.4 mm) is suitable.

The filtering foam which constitutes the prefiltration unit 24 may also be adapted to a given dust-laden atmosphere. This foam is generally also of grade 45, but it is possible to use concentric rings threaded one into the other as shown as a dash-dotted line to produce a filtration effect increasing progressively before the air reaches the central passage opening 25.

After having gone through the central passage opening 25, air enters the central passage 21, and then the central air inlet channel 12 from which the centrifugal effect of rotation and the curved flank of the central projection tend to spread it in a radial direction in the free space 14. From the latter the air can reach the outlet holes 16 only by passing through, counter-current fashion, the thickness of the filtering foam crown 11 where the breathable dust is retained.

Again, if dust of particle sizes in excess of a value of 5 microns allowed for breathable dust has reached the free space 14, it may remain in the latter without impairing the operation of the collector.

As a result of the new design of the collector, the latter can operate efficiently and retain in crown 11 the so-called breathable dust, for example in the range of 0.5 to 5 microns, in an atmosphere heavily laden with a substantial amount of coarser dust. The latter is caught as it passes through by successive means able to contain a substantial volume of said dust.

It will be observed that the annular volume 34 could be filled with a foam ring with open pores of a value greater than 45 to retain the coarser dust, the central opening 25 remaining directly connected to the central air inlet 21 of the cover 15.

FIG. 2 shows a dust collector in every respect similar overall to that of FIG. 1 for which the same references have been used to denote identical parts. It will not be described again in its entirety. Only the differences will be stressed which are designed to simplify the structure of the collector whilst maintaining, or even improving, its efficiency.

The opening 32 of the hood 30 opens inwardly into a hollow cylinder 39 concentric with the axis 20 so as to better channel the dust to be retained towards the filtering mass 29. The auxiliary cup 28 has its dimension in the axial direction increased and the filtering foam 29 occupies only about half the length of said cup on the prefiltration unit 24 side.

The boss 18 and the annular volume 34 shown in FIG. 1 have been omitted, and the prefiltration unit 24 extends into contact with the outer face of the outermost wall 17 of the cover 15.

The auxiliary cup 28 of which the impact wall 27 forms a part has a side wall which is extended from said impact wall 27 as a hollow cylinder in the direction of the cover 15, in the outer peripheral space 33, over a substantial portion of the length of the prefiltration unit 24. Moreover, at least at that part where it is surrounded by the extended cylindrical side wall 40 of the auxiliary cup 28, this prefiltration unit 24 has a reduced diameter so that said side wall 40 surrounds it without touching it. Air laden with less coarse particles of dust is thus able to flow into the peripheral space 33, following the extended side wall 40, and go through the prefiltration unit 24, if need be going up into the annular space 41 provided internally between said side wall 40 and the external side face of the prefiltration unit 24, as this annular space 41 is in communication with the peripheral space 33.

Moreover, it will suffice to provide on the cover 15, in its side wall, a single air outlet hole 16.

I claim:

1. A portable individual dust collector comprising:
   a cover having a main longitudinal axis, a central air inlet around said axis and at least one lateral air outlet;
   a rotatable cup mounted within said cover for rotation about said axis and positioned so that the air flowing through said inlet is directed into said cup;
   a crown of filtering foam with a central air inlet channel contained within said cup;
   a hood supported by said cover and having a central inlet opening around said axis; and
   a prefiltration unit contained in said hood and disposed upstream of said central air inlet of said cover, said unit ending in a first outermost face spaced from said cover, said prefiltration unit having a central passage connected to said central air inlet of said cover, said unit being supported within said hood so that an external peripheral space is defined thereabout and said first outermost face of the said unit being lined with a gas-tight impact wall sealing an end of said central passage, said impact wall being the bottom wall of an auxiliary cup facing said central inlet opening of said hood, said gas-tight impact wall causing the air flowing through said central inlet opening of said hood to first flow generally radially outward, then longitudinally in said external peripheral space, and then generally radially into said unit.

2. A collector according to claim 1, wherein the prefiltration unit is shaped and supported within the hood to define with said hood and the cover an annular space which communicates with the external peripheral space and surrounds said central passage.

3. A collector according to claim 2, wherein the cover has an outermost face provided inside the hood with a central boss surrounding the general axis through which the central passage passes, said central boss supporting the prefiltration unit and having in the direction transverse to said axis a size smaller than that of the hood so that it defines with the latter, in a transverse direction, the annular space.

4. A collector according to claim 3, wherein the central boss ends in an outermost face with an axially projecting stub which surrounds the central passage, and face and said projecting stub supporting the prefiltration unit, the central passage of the unit being arranged to receive the projecting stub.

5. A collector according to claim 4, wherein the outer face of the outermost wall of the cover carries a collar for mounting the hood concentric with the general axis, the collar defining with the prefiltration unit a throttled annular passage for communication between the peripheral space and the annular space.

6. A collector according to claim 1, wherein the auxiliary cup contains a filtering foam.

7. A collector according to claim 1, wherein the crown of filtering foam is contained in the rotatable cup and defined with the inner face of the bottom of said cup of a free space.

8. A collector according to claim 7, wherein said inner face has a central projection with a curved concave flank which extends into the central air intake channel of the crown of filtering foam coaxially with said crown.

9. A collector according to claim 1, wherein the inner face of the outermost wall of the cover has an inner extension around the central air inlet which extends into the central channel of the crown.

10. A collector according to claim 1, wherein the impact wall supports a rod which extends through the central opening of the hood and which is provided at its external free end with a mask extending in front of the outermost face of said hood.

11. A collector according to claims 1 or 7, wherein the auxiliary cup has a wall extending from its bottom impact wall towards the cover and defining a hollow cylinder extending in the external peripheral space and surrounding the prefiltration unit without touching it over a substantial part of the length of said unit, said side wall defining with the outer side face of said prefiltration unit and annular space in communication with the peripheral space.

* * * * *